United States Patent
Thienphrapa et al.

(10) Patent No.: US 11,344,222 B2
(45) Date of Patent: May 31, 2022

(54) SYSTEMS AND METHODS FOR DETERMINING THE POSITION OF A NON-SHAPE-SENSED GUIDEWIRE WITH A SHAPE-SENSED CATHETER AND FOR VISUALIZING THE GUIDEWIRE

(71) Applicant: KONINKLIJKE PHILIPS N.V., Eindhoven (NL)

(72) Inventors: Paul Thienphrapa, Cambridge, MA (US); Torre Michelle Bydlon, Melrose, MA (US); Molly Lara Flexman, Melrose, MA (US); Alexandru Patriciu, Belmont, MA (US); Ashish Panse, Burlington, MA (US); Sean Joseph Kyne, Brookline, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 410 days.

(21) Appl. No.: 16/462,388

(22) PCT Filed: Dec. 13, 2017

(86) PCT No.: PCT/EP2017/082594
§ 371 (c)(1),
(2) Date: May 20, 2019

(87) PCT Pub. No.: WO2018/108993
PCT Pub. Date: Jun. 21, 2018

(65) Prior Publication Data
US 2019/0313940 A1    Oct. 17, 2019

Related U.S. Application Data

(60) Provisional application No. 62/433,267, filed on Dec. 13, 2016.

(51) Int. Cl.
*A61B 5/00* (2006.01)
*A61B 5/06* (2006.01)
(Continued)

(52) U.S. Cl.
CPC .............. *A61B 5/064* (2013.01); *A61B 5/066* (2013.01); *A61B 5/6851* (2013.01); *A61B 90/39* (2016.02);
(Continued)

(58) Field of Classification Search
CPC ......... A61B 5/064; A61B 90/39; A61B 5/066; A61B 5/6851; A61B 2034/2061;
(Continued)

(56) References Cited

U.S. PATENT DOCUMENTS

2010/0274270 A1   10/2010   Patel et al.
2013/0090530 A1    4/2013   Ramamurthy et al.
(Continued)

OTHER PUBLICATIONS

International Search Report—PCT/EP2017/082594, filed Dec. 13, 2017.

*Primary Examiner* — Joel Lamprecht

(57) ABSTRACT

A system and method for determining the position of a non-shape-sensed guidewire (102) and for visualizing the guidewire. The system includes a shape-sensed catheter (104) having a lumen (103) that is configured to receive the non-shape-sensed guidewire. A measurement module (122) is configured to measure a distance that the non-shape-sensed guidewire moves. The measurement module may receive signals from a sensor (124) associated with a measurement assembly that is configured to receive at least a portion of the non-shape-sensed guidewire and/or the shape-sensed catheter. A location module (126) is configured to determine a position of the non-shape-sensed guidewire. The system is configured to generate a virtual image (101) of the guidewire, including a portion of the non-shape- (Continued)

sensed guidewire that does not extend along a shape-sensing optical fiber.

18 Claims, 15 Drawing Sheets

(51) Int. Cl.
*A61B 90/00* (2016.01)
*G01L 1/24* (2006.01)
*A61B 34/20* (2016.01)

(52) U.S. Cl.
CPC ...... *G01L 1/246* (2013.01); *A61B 2034/2061* (2016.02)

(58) Field of Classification Search
CPC ...... A61B 2090/376; A61B 2034/2051; A61B 34/20; A61B 2034/2065; A61B 2034/2055; A61B 2505/05; A61B 2562/0233; A61B 5/065; A61B 5/6852; G01L 1/246; A61M 25/09041; A61M 2025/0166
See application file for complete search history.

(56) References Cited

U.S. PATENT DOCUMENTS

| | | |
|---|---|---|
| 2016/0228200 A1 | 8/2016 | Denissen et al. |
| 2017/0215973 A1 | 8/2017 | Flexman et al. |
| 2017/0281293 A1 | 10/2017 | Verstege et al. |

SYSTEMS AND METHODS FOR DETERMINING THE POSITION OF A NON-SHAPE-SENSED GUIDEWIRE WITH A SHAPE-SENSED CATHETER AND FOR VISUALIZING THE GUIDEWIRE

CROSS-REFERENCE TO PRIOR APPLICATIONS

This application is the U.S. National Phase application under 35 U.S.C. § 371 of International Application Serial No. PCT/EP2017/082594, filed on Dec. 13, 2017, which claims the benefit of U.S. Patent Application No. 62/433,267, filed on Dec. 13, 2016. This application is hereby incorporated by reference herein.

BACKGROUND

Technical Field

This disclosure relates to medical instruments and more particularly to systems having shape sensing optical fibers in catheters for determining the position of a non-shape-sensed guidewire and visualizing the guidewire.

Description of the Related Art

A medical device may be enabled with shape sensing by embedding an optical fiber(s) within the device. Optical shape sensing (OSS) or Fiber-Optical RealShape™ (hereinafter, "FORS™") employs light along an optical fiber for device localization and navigation during surgical intervention. One principle involved makes use of distributed strain measurement in the optical fiber using characteristic Rayleigh backscatter or controlled grating patterns. Multiple optical fibers can be used together to reconstruct a 3D shape, or a single optical fiber with multiple cores that may also be helixed for a lower-profile sensor. The shape along the optical fiber begins at a specific point along the sensor, known as the launch or z=0, and the subsequent shape position and orientation are relative to that point. FORS™ fibers can be integrated into medical devices to provide live guidance of the devices during minimally invasive procedures.

The inclusion of a FORS™ shape sensing device permits the determination of the shape of the device and a visualization of a virtual device without requiring an imaging device such as an x-ray imaging device. However, the shape sensing device requires customizing a mechanical design of the device to add an additional lumen for the fiber. Adding the fiber also adds cost to the device and necessitates the use of an additional shape sensing system.

The shape of a non-shape-sensed device, such as a guidewire that is received in a catheter having FORS™ shape sensing, will be defined by the shape of the catheter for the length over which the devices overlap. It would be advantageous to utilize the FORS™ catheter to determine a position of the non-shape-sensed guidewire in the catheter and to accurately visualize the non-shape-sensed guidewire. Furthermore, it would be advantageous to visualize the portion of the non-shape-sensed guidewire that does not overlap with the FORS™ catheter.

SUMMARY

In accordance with the present principles, a system for determining a position of a non-shape-sensed guidewire is provided. The system includes a non-shape-sensed guidewire. The system also includes a shape-sensing catheter having a lumen, wherein the non-shape-sensed guidewire is received in the lumen. A measurement assembly is configured to receive at least a portion of the non-shape-sensed guidewire and/or the shape-sensing catheter. A measurement module is configured to measure a distance that the non-shape-sensed guidewire moves in the measurement assembly. A location module is configured to determine a position of the non-shape-sensed guidewire based on the distance that the non-shape-sensed guidewire moves determined by the measurement module.

In another embodiment, a system for determining a position of a non-shape-sensed guidewire includes a non-shape-sensed guidewire. A temperature control device associated with the non-shape-sensed guidewire is configured to heat or cool the non-shape-sensed guidewire to provide a predetermined temperature profile along the non-shape-sensed guidewire. A shape-sensing catheter having a lumen receives the non-shape-sensed guidewire in the lumen, the shape-sensing catheter has a shape-sensing optical fiber that is configured to sense temperature along the non-shape-sensed guidewire. A location module is configured to receive signals from the shape-sensing optical fiber concerning the temperature along the non-shape-sensed guidewire and compare a sensed temperature profile to the predetermined temperature profile to determine a position of the non-shape-sensed guidewire.

In another embodiment, a system for determining a position of a non-shape-sensed guidewire includes a non-shape-sensed guidewire. A vibration device associated with the non-shape-sensed guidewire is configured to generate a predetermined vibration profile along the non-shape-sensed guidewire. The vibration device has a known position. A shape-sensing catheter having a lumen receives the non-shape-sensed guidewire in the lumen. A hub is configured to receive the shape-sensing catheter and secure a position of the shape-sensing catheter. The hub includes a sensor having a known position that is configured to sense the vibration along the non-shape-sensed guidewire. A location module is configured to receive signals from the sensor concerning the vibrations and determine a time period between the generation of vibrations by the vibration device to a sensing of the vibrations by the sensor to determine a position of the non-shape-sensed guidewire.

In another embodiment, a system for determining the position of a non-shape-sensed guidewire includes a non-shape-sensed guidewire. A shape-sensing catheter having a lumen, receives the non-shape-sensed guidewire in the lumen. A measurement module is configured to detect the vibration, shape, or axial strain on a distal tip of the shape-sensing catheter to determine the position of the non-shape-sensed guidewire and/or movement thereof.

In another embodiment, a method for determining the position of a non-shape-sensed guidewire is provided. The method includes the steps of receiving the non-shape-sensed guidewire in a lumen of a shape-sensing catheter; receiving at least a portion of the non-shape-sensed guidewire and/or the shape-sensing catheter in a measurement assembly; measuring a distance that the non-shape-sensed guidewire moves in the measurement assembly by a measurement module; and determining a position of the non-shape-sensed guidewire by a location module based on the distance that the non-shape-sensed guidewire moves in the measurement assembly.

In another embodiment, a method for determining the position of a non-shape-sensed guidewire is provided. The method includes the steps of receiving the non-shape-sensed guidewire in a lumen of a shape-sensing catheter; heating or cooling the non-shape-sensed guidewire by a temperature control device to provide a predetermined temperature profile along the non-shape-sensed guidewire; sensing a temperature along the non-shape-sensed guidewire by a shape-sensing optical fiber of the shape-sensing catheter; and comparing a sensed temperature along the non-shape-sensed guidewire with the predetermined temperature profile to determine a position of the non-shape-sensed guidewire.

In another embodiment, a method for determining the position of a non-shape-sensed guidewire is provided. The method includes the steps of receiving the non-shape-sensed guidewire in a lumen of a shape-sensing catheter; receiving the shape-sensing catheter and the non-shape-sensed guidewire in a hub having a sensor; generating a predetermined vibration profile along the non-shape-sensed guidewire by a vibration device having a known position; sensing the vibration along the non-shape-sensed guidewire by the sensor; and determining a time period between the generation of the vibrations by the vibration device and the sensing of the vibrations by the sensor to determine a position of the non-shape-sensed guidewire.

In another embodiment, a method for determining the position of a non-shape-sensed guidewire is provided. The method includes the steps of receiving the non-shape-sensed guidewire in a lumen of a shape-sensing catheter; and sensing vibration, shape, or axial strain on a distal tip of the shape-sensing catheter to determine the position of the non-shape-sensed guidewire and/or movement thereof.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
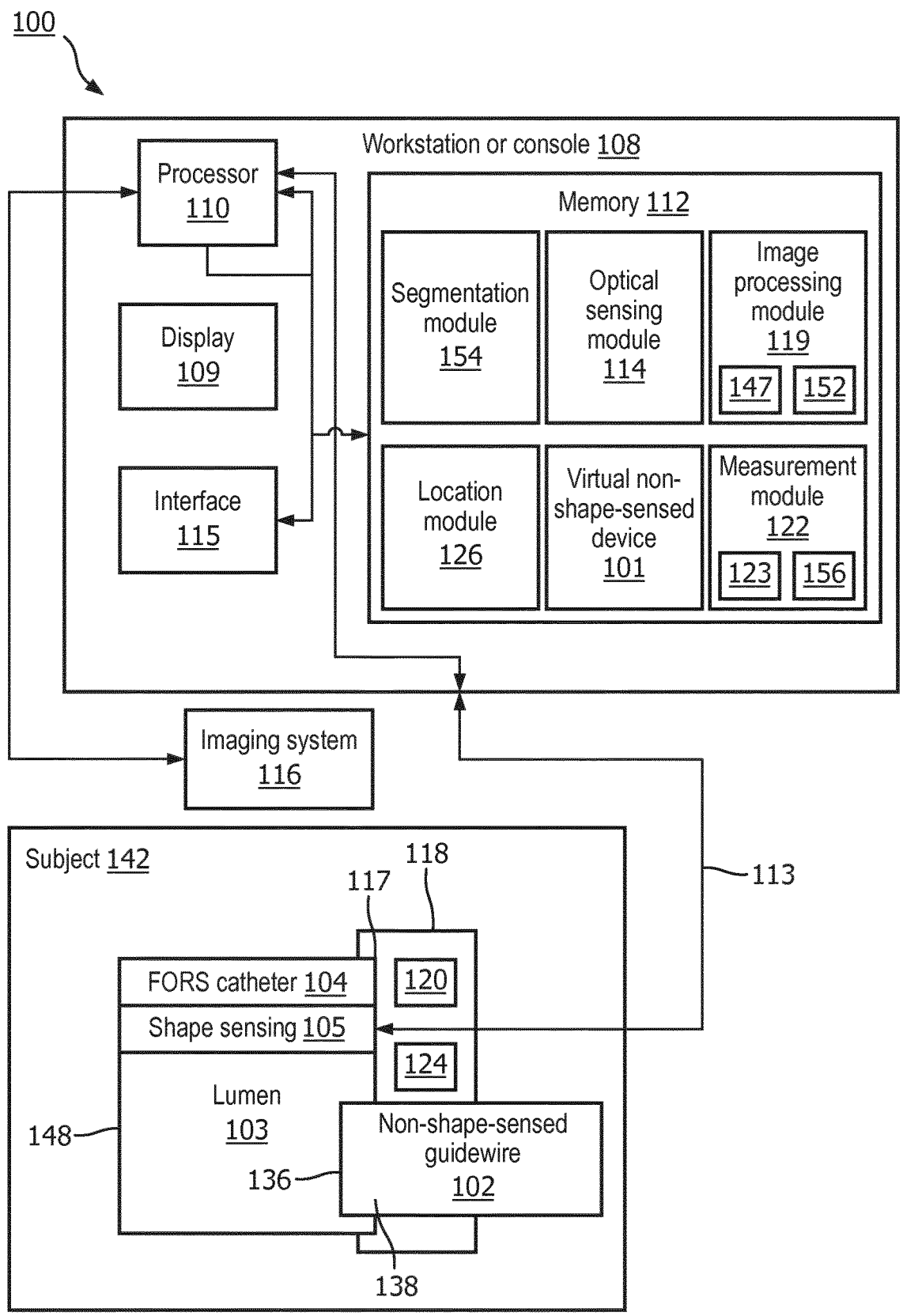
FIG. 1 is a block/flow diagram showing a system for determining the position of a non-shape-sensed guidewire in accordance with one embodiment.

In accordance with the present principles, a system for determining the position of a non-shape-sensed guidewire utilizing a FORS™ catheter and for visualizing the non-shape-sensed guidewire is provided. The system is configured to determine the position of the non-shape-sensed guidewire by utilizing a FORS™ catheter which has a lumen that is configured to receive the non-shape-sensed guidewire. The system may include a measurement assembly which is configured to receive at least a portion of the non-shape-sensed guidewire and/or the FORS™ catheter. A measurement module is configured to measure a distance that the non-shape-sensed guidewire moves in the measurement assembly. A location module is configured to determine a position of the non-shape-sensed guidewire based on the distance that the non-shape-sensed guidewire moves that is determined by the measurement module.

The system is also configured to detect the presence of the guidewire within the proximal end of the FORS™ catheter, detect the presence of the non-shape-sensed guidewire within other portions of the FORS™ catheter and to detect and measure the distance that the non-shape-sensed guidewire moves. The system may provide feedback to the user concerning the detection and/or measurement of the guidewire's movement and position.

The system provides improvements for the visualization of the non-shape-sensed guidewire during an interventional procedure by the generation of a virtual guidewire. The virtual guidewire that is generated by the system also includes a portion of the non-shape-sensed guidewire that does not extend along a FORS™ fiber, such as the portion that protrudes from a distal tip of the FORS™ catheter.

The system permits the guidewire to be a conventional commercial over the counter guidewire which does not require a FORS™ shape sensing system to be incorporated in the device in order for its shape, position and orientation to be tracked and visualized.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems and procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 for determining the position of a non-shape-sensed guidewire 102 that is received by a shape-sensing catheter 104, such as a FORS™ catheter, is illustratively shown in accordance with one embodiment. While the non-shape-sensed interventional device is illustratively described as being a guidewire 102, in other embodiments, the device may be any medical device that is configured to be received in the lumen of another medical device. For example, the non-shape-sensed device may be a k-wire, a syringe tip, suture thread, or other such component. Additionally, while the FORS™ device is illustratively described as being a FORS™ catheter 104, the FORS™ device may be any other FORS™ device that includes a lumen 103 which may receive a guidewire or other device configured to be received in a lumen. For example, the FORS™ device may be any "over-the-wire" device having a lumen, such as a sheath, a probe, an endograft deployment device, a robot, an electrode, a filter device, a balloon device, a graft, a stent, a drill, and awl, a screwdriver or other similar component. The devices may be robotically or manually controlled.

System 100 may include a workstation or console 108 from which a procedure is supervised and/or managed. Workstation 108 preferably includes one or more processors 110 and memory 112 for storing programs and applications.

Memory 112 may store an optical sensing module 114 configured to interpret optical feedback signals from a shape sensing device or FORS™ system 105. The FORS™ catheter 104 is configured to receive the FORS™ system 105 therethrough. The optical sensing module 114 is configured to use the optical signal feedback (and any other feedback) to reconstruct deformations, deflections and other changes associated with shape sensed devices.

The shape sensing system 105 includes one or more optical fibers 113 which may be arranged in a set pattern or patterns. The optical fibers 113 connect to the workstation 108 through cabling. The cabling may include fiber optics, electrical connections, other instrumentation, etc., as needed.

System 105 with fiber optics may be based on fiber optic Bragg grating sensors, Rayleigh scattering, or other types of scattering. Inherent backscatter in conventional optical fiber can be exploited, such as Raleigh, Raman, Brillouin or fluorescence scattering. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, or in multiple single-core fibers arranged together, the 3D shape and dynamics of the surface of interest can be followed.

A fiber optic Bragg grating (FBG) system may also be employed for system 105. FBG is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

Fresnel reflection at each of the interfaces where the refractive index is changing is measured. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors.

Incorporating three or more cores permits a three dimensional form of such a structure to be precisely determined. From the strain measurement, the curvature of the structure can be inferred at that position. From the multitude of measured positions, the total three-dimensional form is determined. A similar technique can be used for multiple single-core fibers configured in a known structure or geometry.

The workstation 108 includes a display 109 for viewing internal images of a subject 142 or volume. The workstation 108 includes an image processing module 119 that is configured to generate a virtual representation 101 of the non-shape-sensed guidewire as an overlay on medical images such as x-ray images, computed tomography (CT) images, magnetic resonance images (MRI), real-time internal video images or other images as collected by an imaging system 116 in advance or concurrently. The imaging system 116 may be an x-ray imaging device or other known imaging device. The imaging device is configured to acquire images of the subject 142.

Display 109 may also permit a user to interact with the workstation 108 and its components and functions, or any other element within the system 100. This is further facilitated by an interface 115 which may include a keyboard, mouse, a joystick, a haptic device, or any other peripheral or control to permit user feedback from and interaction with the workstation 108.

In a preferred embodiment, as shown in FIG. 1, the system 100 includes a FORS™ catheter 104 which has a non-shape-sensed guidewire 102 passing therethrough. As shown in FIG. 1, in one embodiment, the system 100 includes a measurement assembly 118 that is configured to receive at least a portion of the non-shape-sensed guidewire 102 and/or the FORS™ catheter 104. In a preferred embodiment, the measurement assembly 118 is positioned adjacent to, or over, a proximal portion of the FORS™ catheter.

Figure 2:
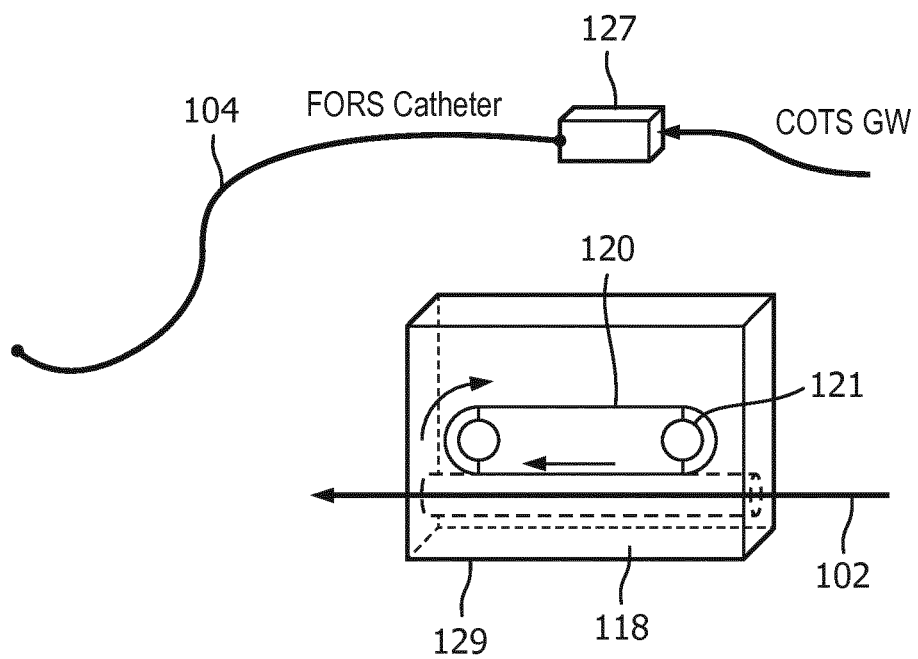
FIG. 2 shows images of the system for determining the position of a non-shape-sensed guidewire in accordance with an embodiment featuring a rotating belt.

In one embodiment, the measurement assembly 118 includes a plurality of movable elements 120 that are configured to contact the non-shape-sensed guidewire 102 and move when the guidewire is advanced or retracted in the lumen 103 of the FORS™ catheter. For example, in the embodiment shown in FIG. 2, the measurement assembly includes a rotating belt 121 which is configured to rotate as the guidewire is advanced or retracted in the lumen 103 of the FORS™ catheter. Image 127 in FIG. 2 shows an overview of the system 100 in this embodiment. Image 129 shows a close up view of the measurement assembly 118 in accordance with this embodiment. The rotating belt 121 preferably functions as a passive conveyor belt which only moves as the non-shape-sensed guidewire is advanced or retracted in the lumen 103 of the FORS™ catheter. In one embodiment, the rotating belt 121 may have an increased length to increase the accuracy of measuring the movement of the belt.

In alternative embodiments, movable elements 120 such as wheels, rollers or balls or other known movable elements may be used instead of a rotating belt 121. Additionally, in certain embodiments, the measurement assembly 118 may include a second set of movable elements (not shown) which are configured to bias the non-shape-sensed guidewire 102 against the movable elements 120 to ensure sufficient contact between the movable elements and the non-shape-sensed guidewire and to minimize friction applied to the non-shape-sensed guidewire.

The measurement assembly 118 also includes a sensor 124 which is associated with the movable elements 120 and is configured to sense movement of the movable elements and send signals concerning the movement that it senses. For example, in the embodiment shown in FIG. 2, the sensor is associated with the rotating belt 121 and senses rotation of the belt in a clockwise and/or counter-clockwise direction.

Figure 3:
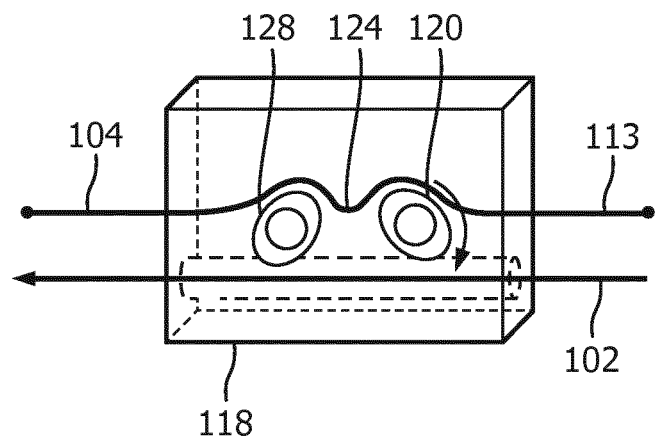
FIG. 3 shows images of the system for determining the position of a non-shape-sensed guidewire in accordance with an embodiment featuring cams.

FIG. 3 shows another embodiment of the system 100 in which the movable elements 120 of the measurement assembly 118 are a pair of rotating cams 128. The cams 128 contact the non-shape-sensed guidewire 102 and are configured to rotate as the guidewire is advanced or retreated. In this embodiment, the sensor 124 comprises a FORS™ fiber which is configured to be deflected as the cams 128 are rotated. In the embodiment shown in FIG. 3, the measurement assembly 118 is configured to receive the FORS™ catheter 104 and at least one of the optical fibers 113 of the FORS™ catheter is configured to be deflected as the cams 128 are rotated. The at least one optical fiber 113 of the FORS™ catheter that is deflected is preferably positioned along the proximal section of the FORS™ catheter 104. However, in alternative embodiments, the measurement assembly 118 may include a second FORS™ fiber that is not part of the FORS™ catheter which is configured to be deflected as the cams 128 are rotated.

The system 100 also includes a measurement module 122 which is configured to receive signals from the sensor 124 and analyze the signals to detect the presence of the guidewire into the proximal end of the FORS™ catheter 104, detect the presence of the non-shape-sensed guidewire within the FORS™ catheter and to detect and measure the distance that the non-shape-sensed guidewire 102 moves.

The movable elements 120 are preferably encoded so that a specific amount of movement of the guidewire 102 results in a specific amount of movement of the movable elements 120. In one embodiment, the measurement module 122 may include conversion data 123 which converts a specific amount of movement of the non-shape-sensed guidewire 102 with a specific degree of movement of the movable elements 120. The conversion data 123 may be obtained in a calibration phase or may be predetermined by the manufacturer. For example, the rotating belt 121 may be configured to rotate a full revolution for every 1 millimeter that a guidewire is advanced or retracted.

Figure 4:
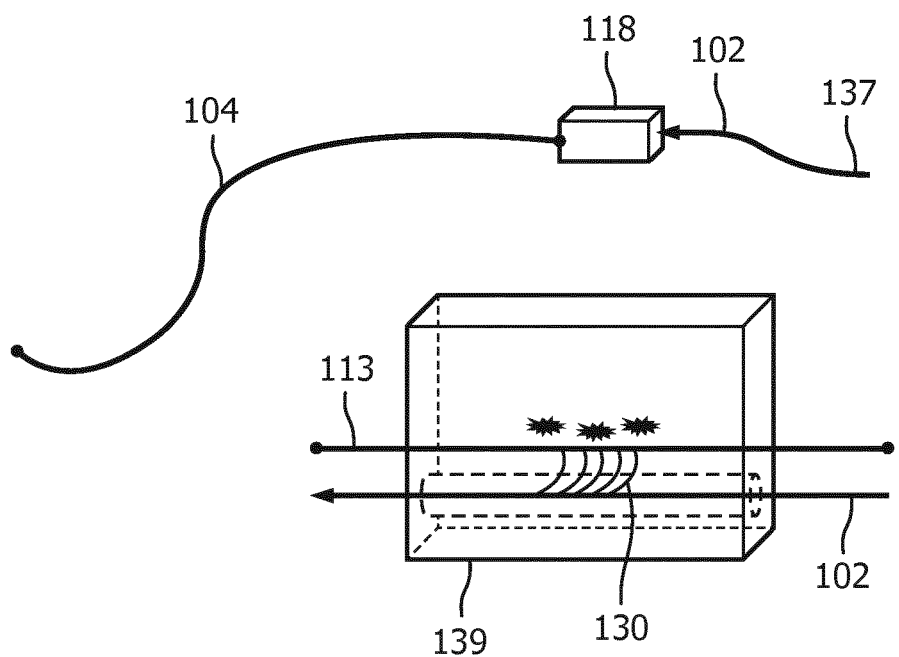
FIG. 4 shows images of a system for determining the position of a non-shape-sensed guidewire in accordance with an embodiment featuring a vibration device in the measurement assembly.

Images 137 and 139 in FIG. 4 show another embodiment of the system 100 in which the measurement assembly 118 includes a vibration mechanism 130 which is configured to interact with the non-shape-sensed guidewire 102 as the guidewire is advanced or retracted in the FORS™ catheter 104. The vibration mechanism 130 is configured to vibrate the FORS™ catheter 104 when the vibration mechanism interacts with the non-shape-sensed guidewire 102.

In this embodiment, the sensor may comprise a FORS™ fiber which is configured to be vibrated by the vibration mechanism 130. A FORS™ system detects the vibration of the FORS™ fiber when it is vibrated and the signal is sent to the measurement module 122. In the embodiment shown in FIG. 4, the measurement assembly 118 is configured to receive the FORS™ catheter 104 and at least one of the optical fibers 113 of the FORS™ catheter is configured to sense vibration caused by the vibration mechanism 130. However, in alternative embodiments, the measurement assembly 118 may include a second FORS™ fiber that is not part of the FORS™ catheter which is configured to sense vibrations by the vibration device 130.

Figure 5:
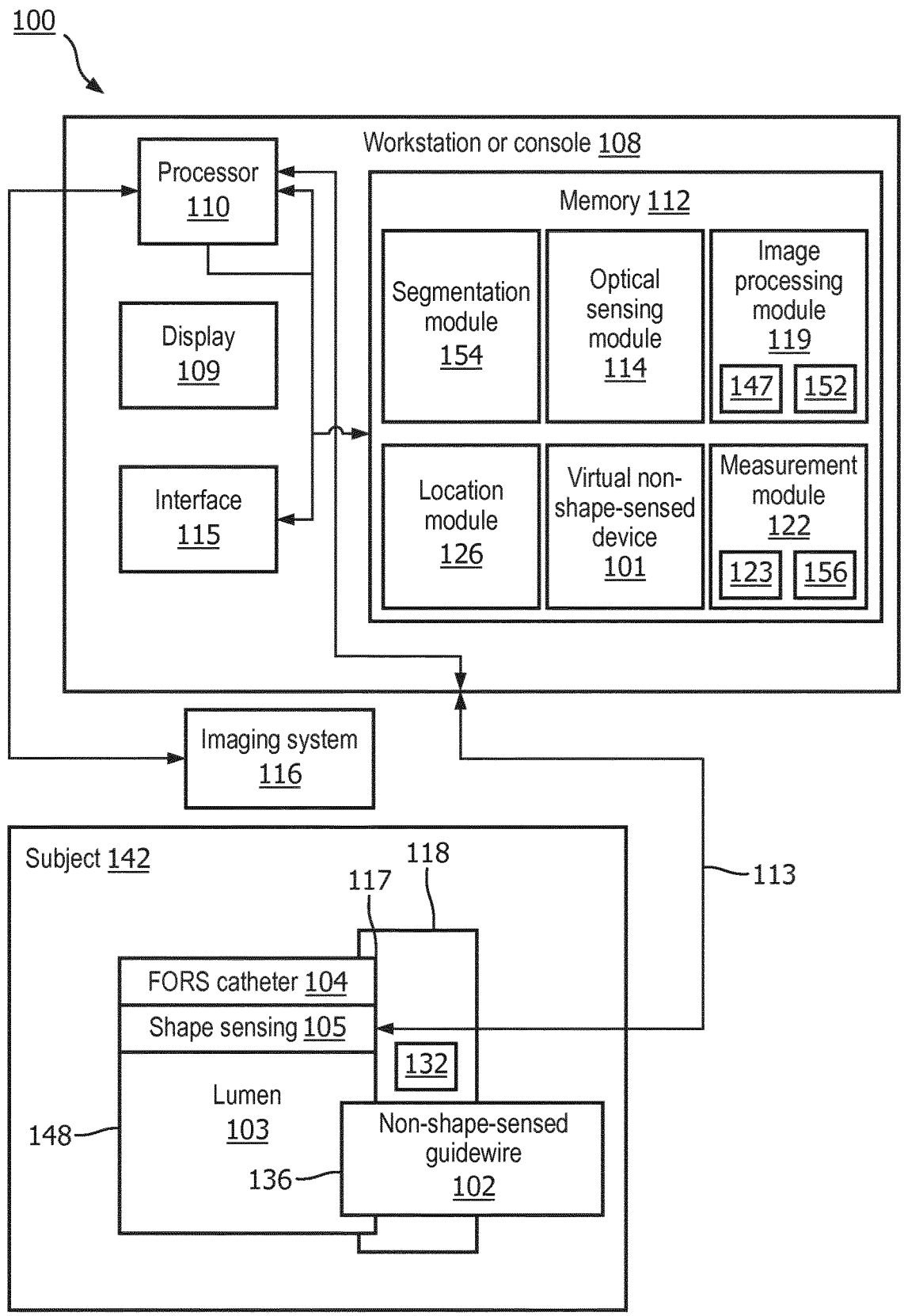
FIG. 5 shows a block/flow diagram showing a system for determining the position of a non-shape-sensed guidewire in accordance with an embodiment featuring a temperature control device in the measurement assembly.

FIG. 5 shows another embodiment of the system 100 in which the measurement assembly 118 includes a temperature control device 132 that is configured to heat or cool the non-shape-sensed guidewire 102 when the guidewire is advanced or retracted a predetermined distance. For example, the temperature control device 132 may include a motion sensor which is configured to trigger the temperature control device to cool or heat the non-shape-sensed guidewire 102 when the non-shape-sensed guidewire 102 is advanced or retracted 1 millimeter. In this embodiment, the sensor 124 may comprise a FORS™ fiber which is configured to sense temperature-induced strain as the guidewire temperature changes. The FORS™ system 105 is configured to detect the temperature-induced strain of the FORS™ fiber as it is heated or cooled. In the embodiment shown in FIG. 5, the measurement assembly 118 is configured to receive the FORS™ catheter 104 and at least one of the optical fibers 113 of the FORS™ catheter is the FORS™ fiber that is configured to sense temperature-induced strain. However, in alternative embodiments, the measurement assembly 118 may include a second FORS™ fiber that is not part of the FORS™ catheter which is configured to sense temperature-induced strain.

Figure 6:
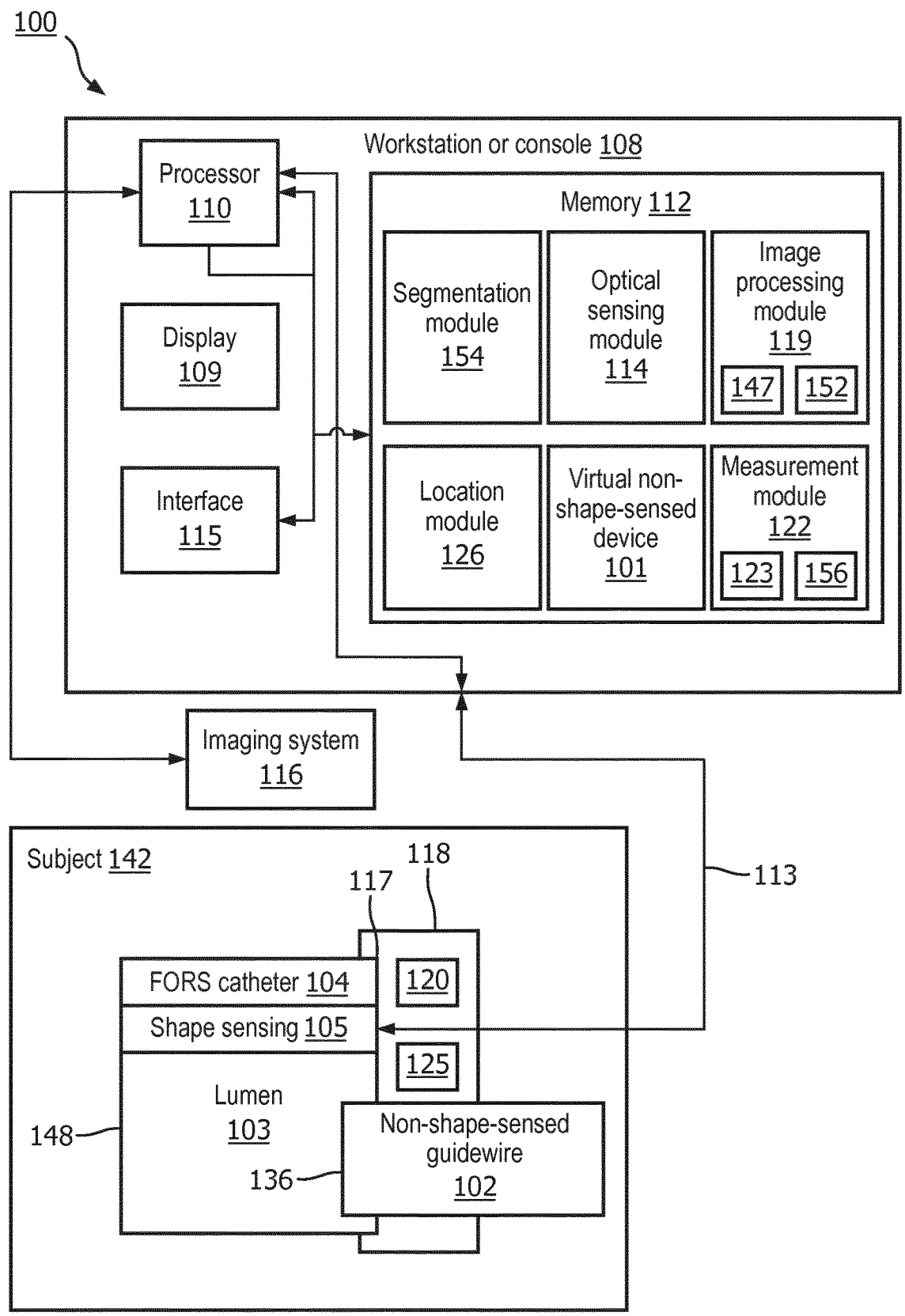
FIG. 6 shows a block/flow diagram showing a system for determining the position of a non-shape-sensed guidewire in accordance with an embodiment featuring an optical tracking device in the measurement assembly.

In another embodiment, shown in FIG. 6, the measurement assembly 118 may include a sensor comprising an optical tracking device 125 that is configured to monitor movement of the non-shape-sensed guidewire and send signals concerning the movement to the measurement module 122. The optical tracking device 125 may be used to read an existing pattern on the non-shape-sensed guidewire 102, or, a retrofit attachment sticker or sleeve could be applied to the guidewire to assist the optical tracking device with monitoring movement. The markers may also serve to calibrate the optical tracking device.

Figure 7:
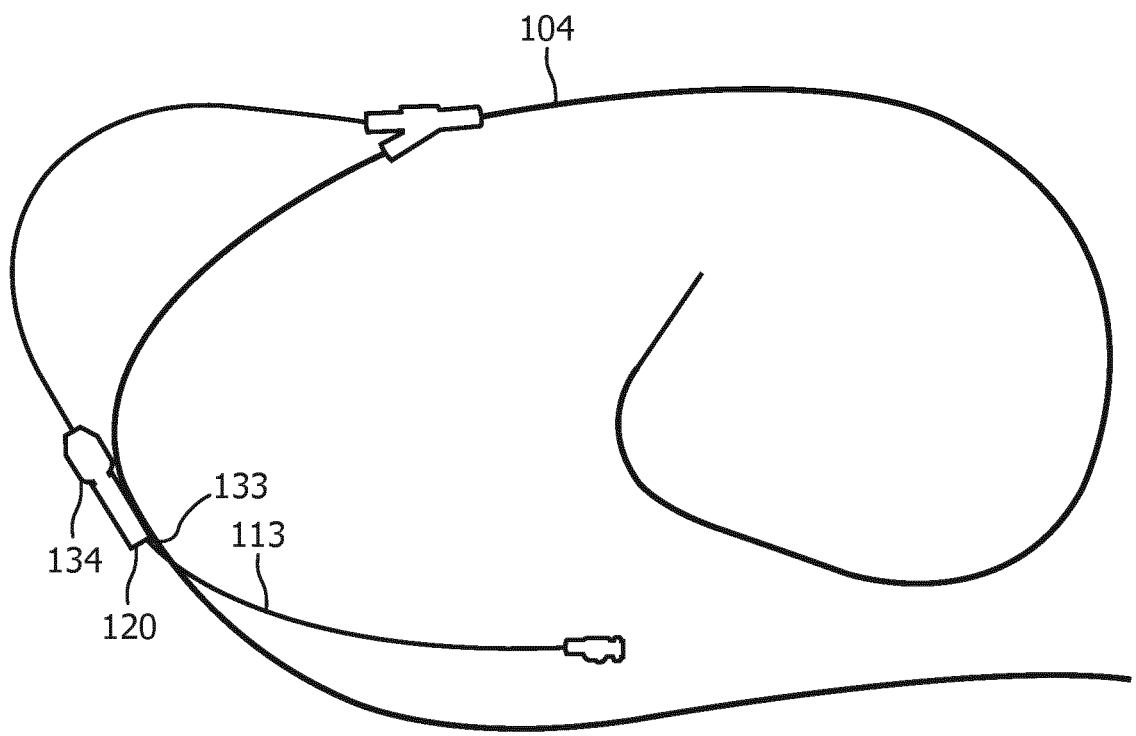
FIG. 7 shows images of the system for determining the position of a non-shape-sensed guidewire in accordance with an embodiment featuring a torquer having a FORS™ fiber.

In the embodiment shown in FIG. 7, the measurement assembly 118 is a torquer 134 that is configured to receive the non-shape-sensed guidewire 102 and to be releasably secured to a position 133 of the guidewire. The torquer 134 includes a FORS™ fiber 113. A location module 126 is configured to receive signals from the FORS™ fiber 113 of the torquer and from the FORS™ fiber of the FORS™ catheter and provide a determination of a position and orientation of the torquer 134 relative to the FORS™ catheter 104. In one embodiment, the torquer 134 is configured to receive the FORS™ catheter 104 and the optical fiber 113 of the FORS™ catheter is the optical fiber which provides a determination of a position and orientation of the torquer relative to the FORS™ catheter. However, in alternative embodiments, the measurement assembly 118 may include a second FORS™ fiber that is not part of the FORS™ catheter which is configured to determine the position and orientation of the torquer 134 relative to the FORS™ catheter. The second FORS™ fiber may be detachably secured to the torquer 134. In other embodiments, a tracking device, such as an optical tracking device, electromagnetic tracking device or other known tracking device may be associated with the torquer 134 and configured to track the position and orientation of the torquer. The FORS™ catheter may include a similar tracking device so that the tracked position of the torquer 134 may be determined relative to the FORS™ catheter 104.

In one embodiment, the location module 126 is configured to determine the position of the torquer 134 with respect to the FORS™ catheter 104 by assuming a straight path distance between the torquer and the FORS™ catheter. In other embodiments, the location module 126 is configured to utilize the five degree of freedom positions and orientations of the torquer 134 and FORS™ catheter 104 to determine the position of the torquer.

The length of the non-shape-sensed guidewire 102 which extends from the fixed position 133 of the guidewire where the torquer 134 is secured may be predetermined. Therefore, the position of the distal tip 136 of the non-shape-sensed guidewire may be determined by the location module 126 using the determined position of the torquer 134 and the predetermined length of the guidewire 102 which extends past the torquer. The stiffness or other mechanical properties of the non-shape-sensed guidewire 102 may be adjusted to provide an improved estimate of the path from the guidewire from the torquer 134 to the FORS™ catheter 104. In the case where the position of the torquer along the guidewire is not predetermined, a registration step can be used. The registration step may include aligning the tip of the two devices and capturing the length or using imaging (x-ray, CT, MRI, ultrasound, etc) to define the distance from the torquer to the tip of the guidewire.

Figure 8:
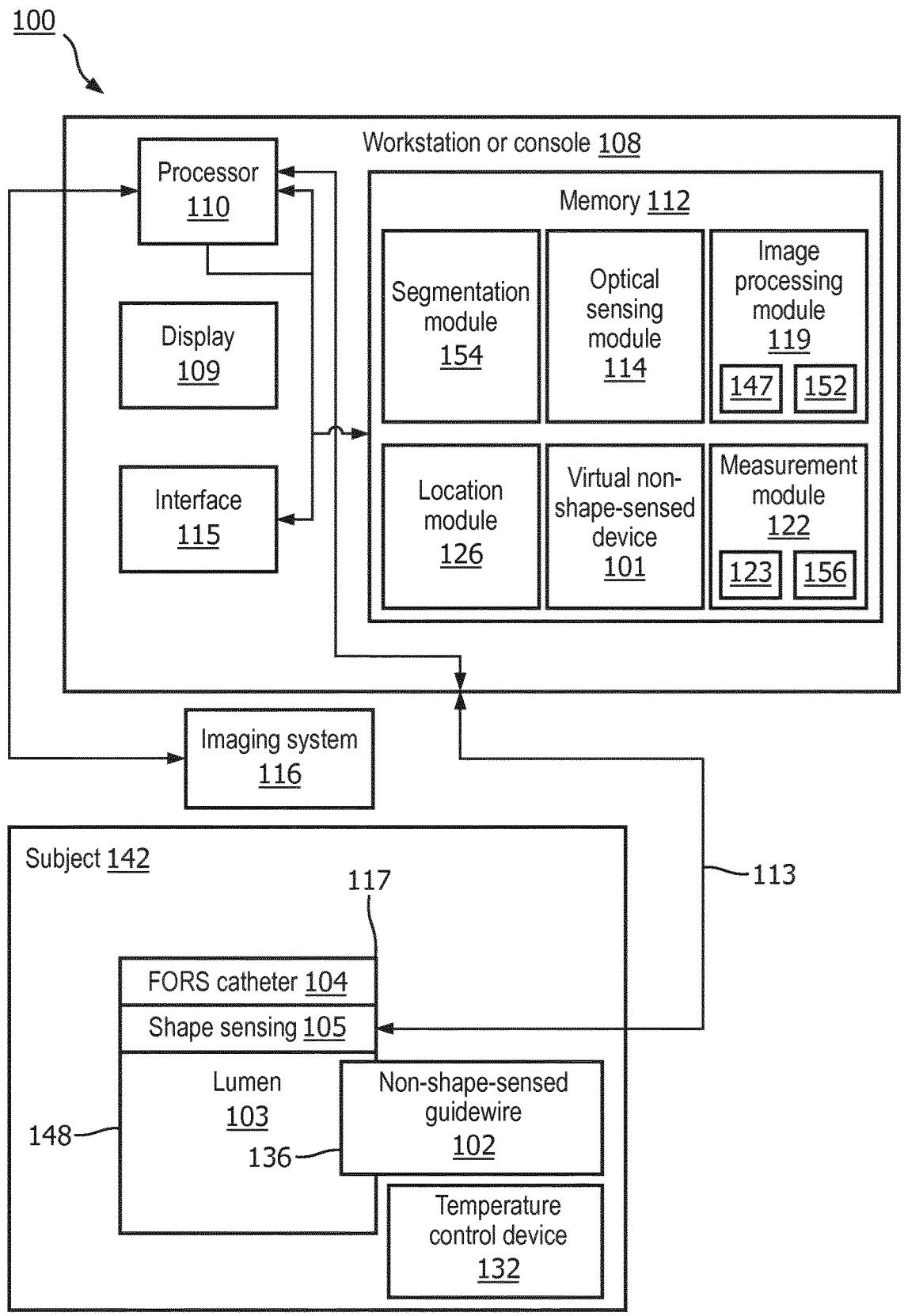
FIG. 8 shows a block/flow diagram showing a system for determining the position of a non-shape-sensed guidewire in accordance with an embodiment featuring a temperature control device.
Figure 9:
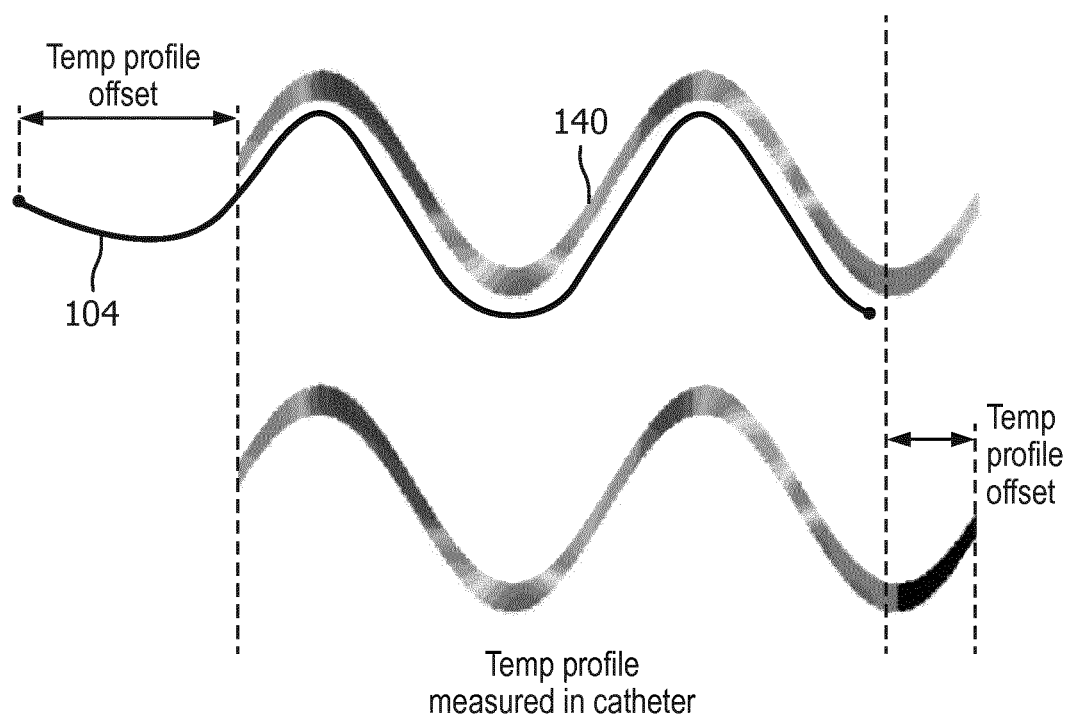
FIG. 9 shows images for the system for determining the position of a non-shape-sensed guidewire in accordance with an embodiment featuring a temperature control device.

FIGS. 8-9 show another embodiment of the system 100 which includes a temperature control device 132. In this embodiment, the temperature control device 132 is configured to heat or cool at least a portion of the non-shape-sensed guidewire 102 to provide a predetermined temperature profile 140 along the length of the non-shape-sensed guidewire. The FORS™ fibers 113 of the FORS™ catheter 104 are configured to sense the temperature along the length of the FORS™ catheter based on temperature-induced strain thereon. The location module 126 is configured to receive signals from the FORS™ system 105 and determine whether there is a match between the measured temperature profile and the predetermined temperature profile. The location module 126 may perform the comparison based on cross correlation or other known matching methods. A matching temperature profile provides a determination of the longitudinal position of the non-shape-sensed guidewire 102 relative to the FORS™ catheter 104.

Figure 10:
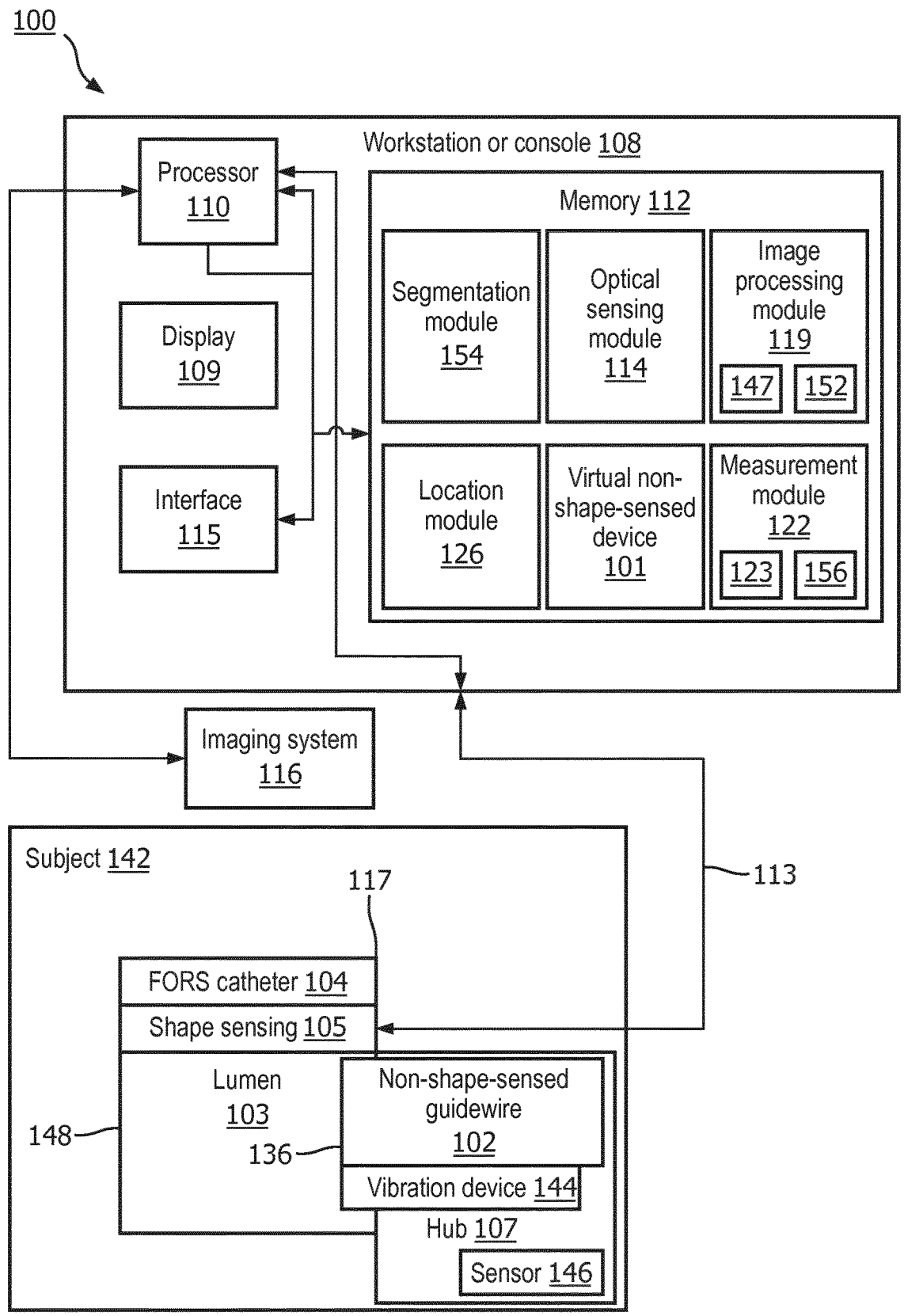
FIG. 10 shows a block/flow diagram showing a system for determining the position of a non-shape-sensed guidewire in accordance with an embodiment featuring a vibration device.

FIG. 10 shows another embodiment of the system 100 which includes a vibration device 144 that is associated with the non-shape-sensed guidewire 102. For example, the vibration device 144 may be incorporated in, or mounted on, the non-shape-sensed guidewire 102. In this embodiment, the vibration device 144 is configured to generate a predetermined vibration profile along the non-shape-sensed guidewire 102. The system also includes a hub 107 that is configured to receive the FORS™ catheter 104 and the non-shape-sensed guidewire 102 and secure a position of the FORS™ catheter and the non-shape-sensed guidewire. The hub includes a sensor 146 having a known position that is configured to sense the vibration along the non-shape-sensed guidewire 102. The location module 126 is configured to receive signals from the sensor 146 concerning the vibrations and determine the time differential between the generation of vibrations by the vibration device 144 and the sensing of the vibrations by the sensor. The location module 126 is configured to analyze the time difference between the generation of the vibrations and the sensing of the vibrations to determine the position of the non-shape-sensed guidewire. The vibration profile created by the vibration device 144 is preferably a distinctive profile to permit the vibrations to be distinguished from ambient noise/vibrations.

In another embodiment, the vibration device is disposed within the measurement assembly 118. The measurement assembly 118 is configured to receive the non-shape-sensed guidewire 102. The measurement assembly 118 also includes a vibration device 144 that is triggered to vibrate as the guidewire passes through the measurement assembly. The vibration created by the vibration device 144 is modulated to correspond to the motion of the non-shape-sensed guidewire 102. The optical fiber(s) 113 of the FORS™ catheter is/are configured to sense the vibration and send the signal to the measurement module 122 to determine a distance that the non-shape-sensed guidewire 102 moves in the measurement assembly.

Figure 11:
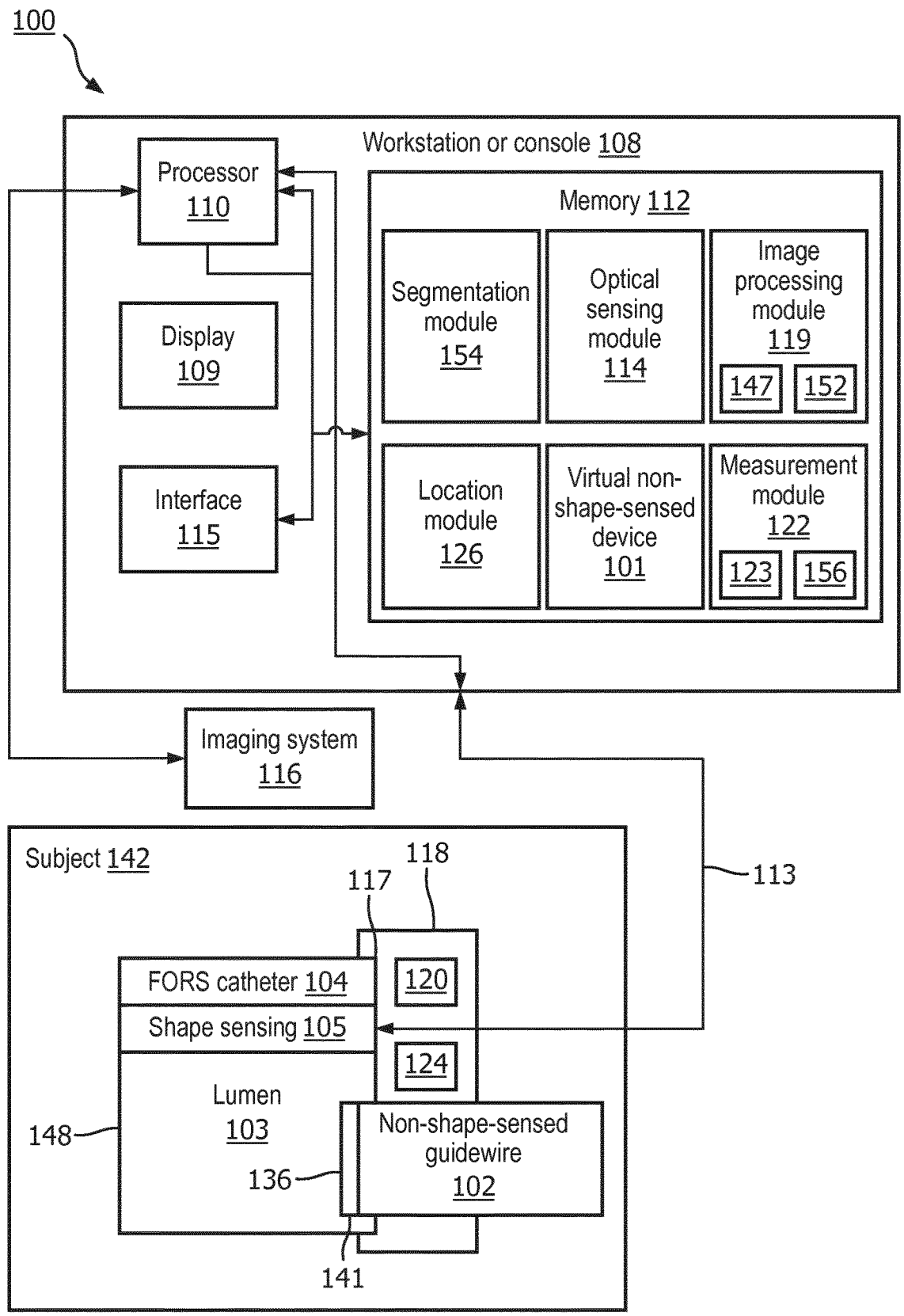
FIG. 11 shows a block/flow diagram showing a system for determining the position of a non-shape-sensed guidewire in accordance with an embodiment featuring mechanical features on the non-shape-sensed guidewire.

In another embodiment shown in FIG. 11, the non-shape-sensed guidewire 102 includes mechanical features 141 which are configured to create a distinct vibration or axial strain on a distal tip 148 of the FORS™ catheter as the guidewire is extended or retracted from the distal tip of the FORS™ catheter. For example, the emergence of the non-shape-sensed guidewire 102 from the distal tip 148 of the FORS™ catheter may cause lateral deflection on the distal end of the FORS™ catheter while the catheter remains in a stationary position in the longitudinal direction. The measurement module 122 is configured to receive the signals from the shape sensing system 105 of the FORS™ catheter 104 due to vibration or axial strain on the distal tip 148 of the FORS™ catheter to detect the presence of the non-shape-sensed guidewire or the movement of the guidewire. For example, the sensing of vibration or axial strain on the distal tip 148 of the FORS™ catheter may indicate the emergence of the non-shape-sensed guidewire 102 from the distal tip 148 of the FORS™ catheter. The mechanical features 141 may be any mating elements, frictional elements or other mechanical elements providing characteristic interactions with each other as generally known in the art.

The location module 126 is configured to receive the measured distance that the non-shape-sensed guidewire 102 moves determined by the measurement module 122 and determine a position of the non-shape-sensed guidewire. The location module 126 is configured to send this position to the image processing module 119 which is configured to generate a virtual non-shape-sensed device 101 on the display 109. The measurement module 122 and the location module 126 are also configured to send feedback to the user concerning the sensed position or movement of the guidewire 102. The feedback may be a visual signal, aural signal, haptic feedback or other feedback known in the art. For example, the location module 126 may be configured to have the system 100 generate a visual signal on the display 109 that the non-shape-sensed guidewire 102 is within the FORS™ catheter 104 when it receives signals from the FORS™ system indicating the presence of the guidewire within the catheter.

While the system utilizes a FORS™ system 105 to measure a portion of the non-shape-sensed guidewire 102 that extends along a FORS™ fiber 113 which enables the determination of the position of the non-shape-sensed guidewire it would also be advantageous to specifically determine the position and orientation of a portion of the non-shape-sensed guidewire that does not extend along a FORS™ fiber. For example, for an embodiment of the system 100 that utilizes shape sensing data from the FORS™ fiber 113 of the FORS™ catheter to measure a position of the non-shape-sensed device, it would be advantageous to measure the position of the non-shape-sensed guidewire which protrudes outside the distal tip 148 of the FORS™ catheter.

Figure 12:
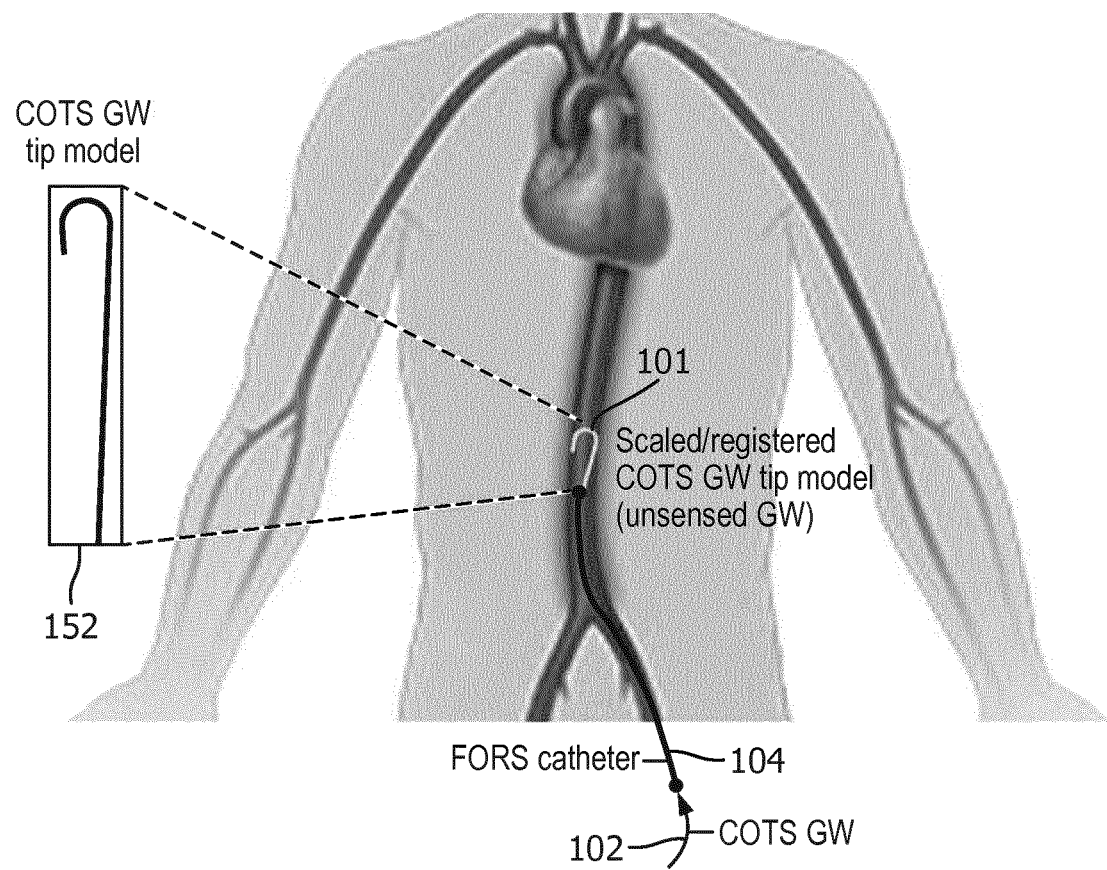
FIG. 12 shows images for the system for determining the position of a non-shape-sensed guidewire in accordance with one embodiment which generates a virtual guidewire utilizing a model.

As shown in FIG. 12, in one embodiment, the image processing module 119 is configured to store a model 152 of the non-shape-sensed guidewire based on known dimensions of the device. The image processing module 119 is configured to generate the virtual guidewire 101 utilizing the model. In one embodiment, the image processing module 119 is configured to receive the most distal position of the non-shape-sensed guidewire that is detected by the location module 126 or the measurement module 122 and position the distal tip of the virtual guidewire 101 in that location. The image processing module 119 is also configured to receive updated positions of the guidewire from the location module 126 based on information sensed by the FORS™ system 105, such as the insertion depth measured by the measurement module 122. The image processing module 119 may also receive information concerning the surrounding anatomical region and the mechanical properties of the guidewire 102 and the FORS™ catheter 104 to further deform the model 152 and the displayed virtual guidewire 101.

In another embodiment, the imaging system 116 is configured to acquire images of the FORS™ catheter 104 and the non-shape-sensed guidewire 102. A segmentation module 154 is configured to segment a portion of the image. For example, the imaging system 116 may be an x-ray imaging system that is configured to acquire 2D fluoroscopy images. The segmentation module 154 is configured to segment a 2D fluoroscopy image of the portion of the non-shape-sensed guidewire which protrudes from the distal tip 148 of the FORS™ catheter. The image processing module 119 is configured to acquire the segmented data and utilize the segmented data in combination with 3D knowledge of the FORS™ catheter tip, to generate a virtual guidewire 101 for the portion of the guidewire 102 that is not shape sensed by the system.

In another embodiment, the system 100 is configured to utilize vibration or axial strain sensed on the distal tip 148 of the FORS™ catheter to determine the position of the non-shape-sensed guidewire 102. For example, the measurement module 122 may include predetermined data 156 concerning the characteristic strain exhibited by different portions of the guidewire on the distal tip 148 of the FORS™ catheter. In one embodiment, the data 156 pertains to lateral motion exhibited by the distal tip 148 of the FORS™ catheter as different portions of the guidewire protrude through the distal tip. The measurement module 122 is configured to analyze the vibration or axial strain on the distal tip 148 of the FORS™ catheter with respect to the predetermined data 156 to determine the portion of the guidewire at the distal tip. The image processing module 119 is configured to generate the virtual guidewire 101 at the position determined by the measurement module 122 based on the determined characteristic strain sensed at the distal tip 148 of the FORS™ catheter.

The distal portion 138 of the non-shape-sensed guidewire may have a distinct shape and mechanical properties which cause characteristic strain or shape deformation on the distal tip 148 of the FORS™ catheter as it emerges from the lumen 103 depending on the orientation of the distal tip of the guidewire as it emerges. The predetermined data 156 may include data concerning the characteristic strain/shape on the distal tip 148 of the FORS™ catheter based on the orientation of the distal portion 138 of the guidewire. The measurement module 122 is configured to determine the orientation of the distal tip 148 of the FORS™ catheter as it emerges from the lumen 103 based on the detected strain at the distal tip.

Furthermore, the location of the strain and shape change detected along the FORS™ catheter may indicate the position of the non-shape-sensed guidewire 102 which protrudes from the catheter. For example, if the portion of the non-shape-sensed guidewire that protrudes from the distal tip 148 of the catheter is bent to the left, more force will be exerted on the right wall of the FORS™ catheter. The image processing module 119 is configured to analyze the shape sensing of the FORS™ catheter 104 determined by the shape sensing system 105 to determine the position of the guidewire that protrudes from the distal tip 148 of the catheter and provide a more accurate positioning of the virtual guidewire 101.

In another embodiment, the image processing module 119 is configured to generate a probabilistic map 147 that extends from the distal tip 148 of the FORS™ catheter based upon the known device length, mechanical properties, x-ray fluoroscopy or other inputs received by the system. The probabilistic map 147 may be a point cloud, a color-coded map, a cone of possible guidewire locations, etc.

Figure 13:
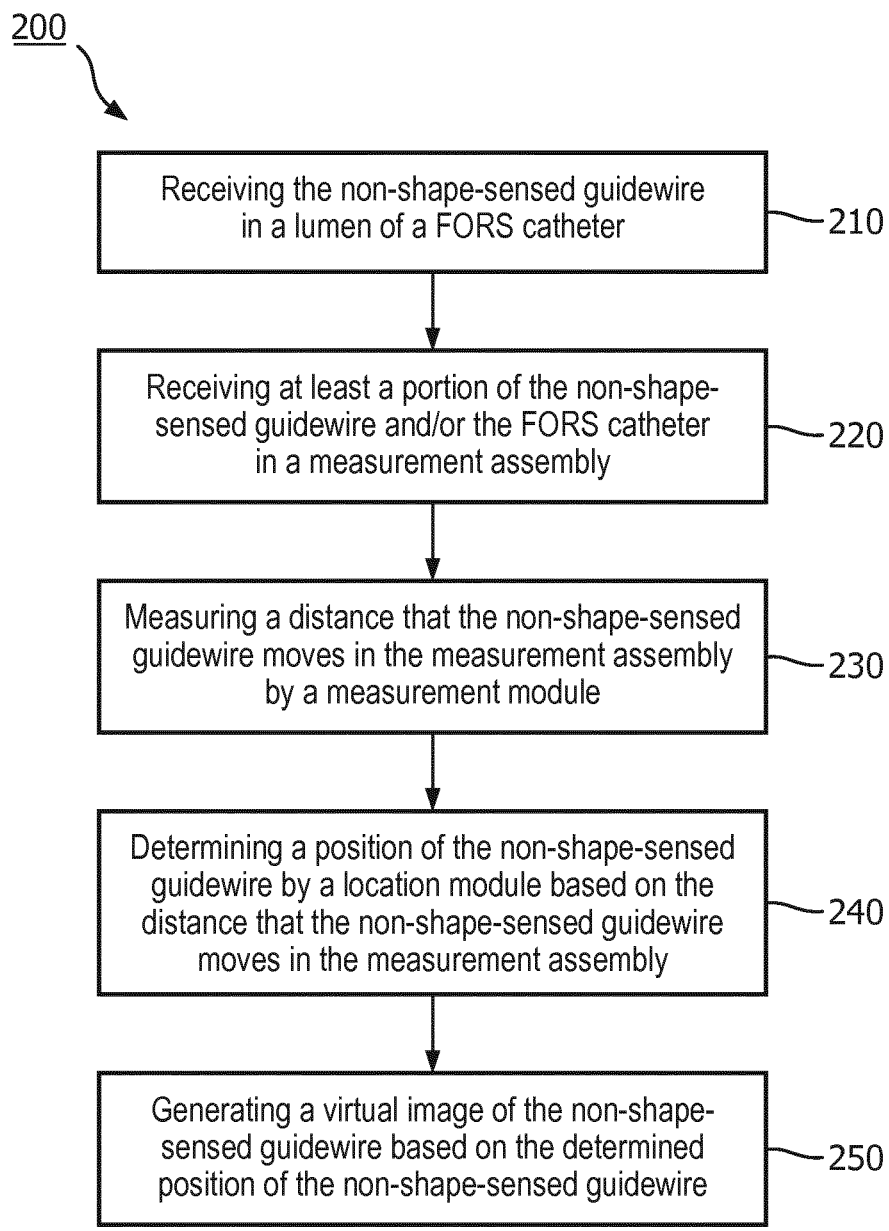
FIG. 13 is a flow diagram showing a method for determining the position of a non-shape-sensed guidewire in accordance with one embodiment.

Referring to FIG. 13, methods 200 for determining the position of a non-shape-sensed guidewire, are illustratively shown in accordance with the present principles. In block 210, the non-shape-sensed guidewire is received in a lumen of a FORS™ catheter. In block 220, at least a portion of the non-shape-sensed guidewire and/or the FORS™ catheter is received in a measurement assembly. In block 230 a distance that the non-shape-sensed guidewire moves in the measurement assembly is measured by a measurement module. In block 240, a position of the non-shape-sensed guidewire is determined by a location module based on the distance that the non-shape-sensed guidewire moves in the measurement assembly.

As previously described, the method may include the further step in block 250 of generating a virtual image of the non-shape-sensed guidewire based on the determined position of the non-shape-sensed guidewire. The generating of a virtual image also includes generating a portion of the non-shape-sensed guidewire that does not extend along a FORS™ fiber as previously described. As previously described, the measurement assembly may include movable elements, such as a rotating belt, wheels, rollers, balls, or at least one cam along with an associated sensor. Alternatively, the measurement assembly may include a vibration device that interacts with the non-shape-sensed guidewire and is configured to generate vibrations on the FORS™ catheter that are sensed by a FORS™ fiber.

In another embodiment, the measurement assembly may include a temperature control device that is configured to heat or cool the non-shape-sensed guidewire and the temperature change is sensed by a FORS™ fiber. In a further embodiment, the measurement assembly comprises a torquer that is secured to a fixed position on the non-shape-sensed guidewire and the torquer includes a FORS™ fiber. The position and orientation of the torquer are determined relative to the FORS™ catheter by analyzing shape sensing information from the FORS™ fiber and the FORS™ catheter.

Figure 14:
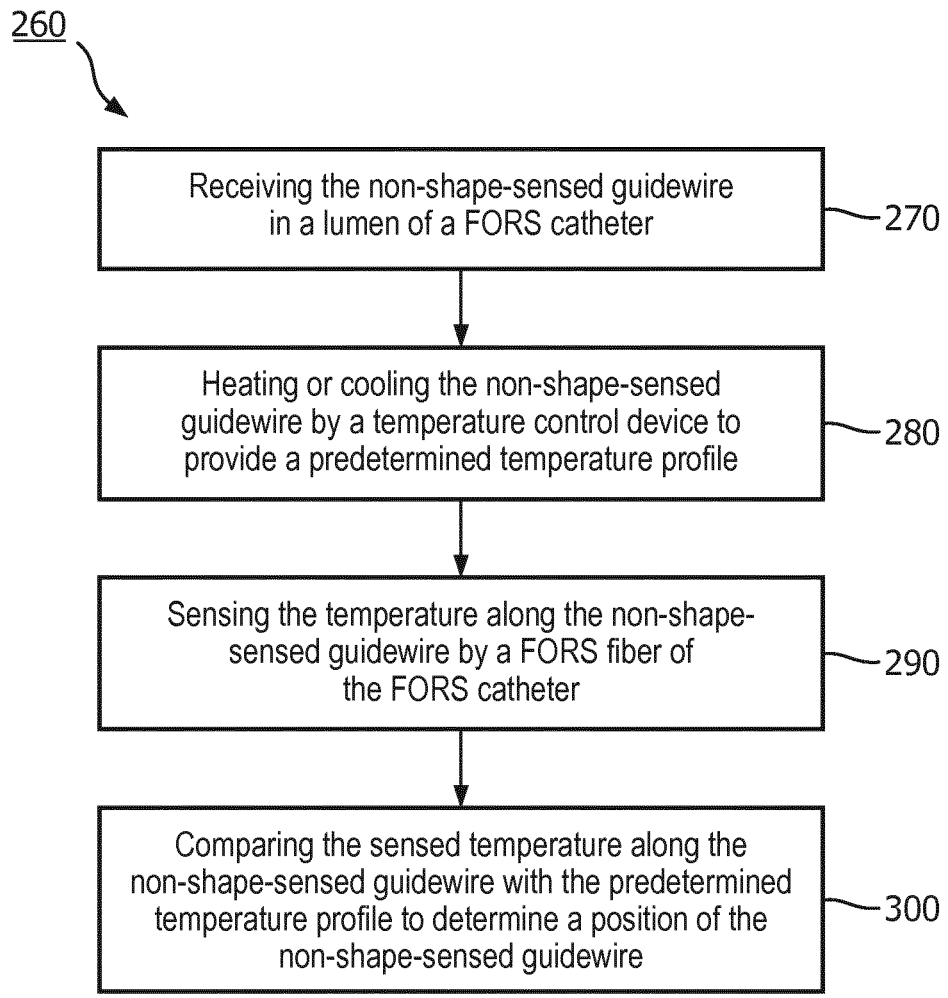
FIG. 14 is a flow diagram showing a method for determining the position of a non-shape-sensed guidewire in accordance with another embodiment.

Referring to FIG. 14, another embodiment for a method 260 for determining the position of a non-shape-sensed guidewire is illustratively shown in accordance with the present principles. In block 270, the non-shape-sensed guidewire is received in a lumen of a FORS™ catheter. In block 280, the non-shape-sensed guidewire is heated or cooled by a temperature control device to provide a predetermined temperature profile along the non-shape-sensed guidewire. In block 290, the temperature is sensed by a FORS™ fiber of the FORS™ catheter along the non-shape-sensed guidewire. In block 300, the sensed temperature along the non-shape-sensed guidewire is compared with a predetermined temperature profile to determine a position of the non-shape-sensed guidewire.

Figure 15:
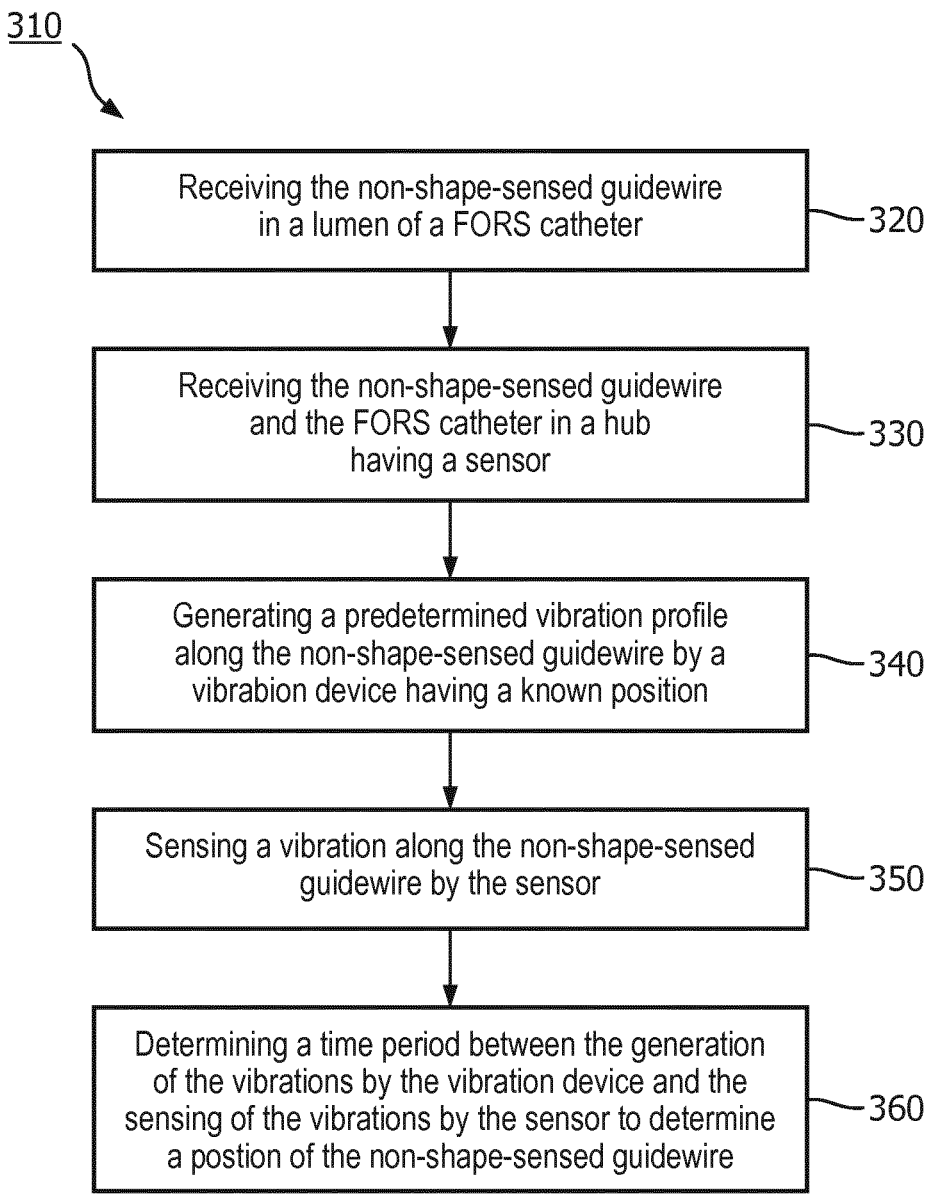
FIG. 15 is a flow diagram showing a method for determining the position of a non-shape-sensed guidewire in accordance with another embodiment.

Referring to FIG. 15, another embodiment for a method 310 for determining the position of a non-shape-sensed guidewire is illustratively shown in accordance with the present principles. In block 320, the non-shape-sensed guidewire is received in a lumen of a FORS™ catheter. In block 330, the FORS™ catheter and non-shape-sensed guidewire are received in a hub having a sensor. In block 340, a predetermined vibration profile is generated along the non-shape-sensed guidewire by a vibration device having a known position. In block 350, the vibration is sensed along the non-shape-sensed guidewire by the sensor. In block 360, the time period between the generation of the vibrations by the vibration device and the sensing of the vibrations by the sensor is determined to determine a position of the non-shape-sensed guidewire.

Figure 16:
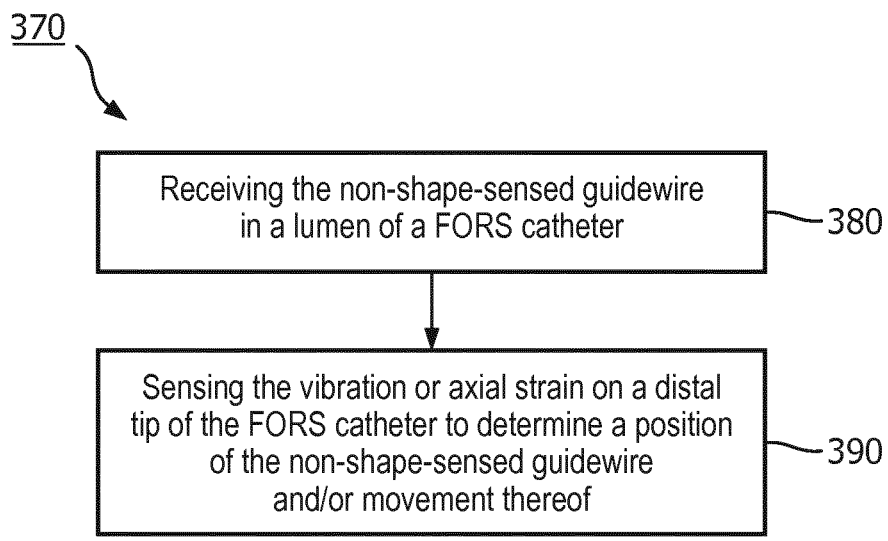
FIG. 16 is a flow diagram showing a method for determining the position of a non-shape-sensed guidewire in accordance with another embodiment.

Referring to FIG. 16, another embodiment for a method 370 for determining the position of a non-shape-sensed guidewire is illustratively shown in accordance with the present principles. In block 380, the non-shape-sensed guidewire is received in a lumen of a FORS™ catheter. In block 390, vibration or axial strain on a distal tip of the FORS™ catheter is sensed to determine a position of the non-shape-sensed guidewire and/or movement thereof.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for systems and methods for determining the position of a non-shape-sensed guidewire with a FORS™ catheter and for visualizing the guidewire (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for determining a position of a guidewire, comprising:
   a guidewire;
   a shape-sensed catheter including a shape sensing optical fiber and having a lumen, wherein the guidewire is received in the lumen;
   a measurement assembly configured to receive at least a portion of the guidewire and/or the shape-sensed catheter, and to monitor movement of the guidewire, wherein the measurement assembly comprises:
      at least one movable element configured to move in response to the guidewire being advanced or retracted in the shape-sensed catheter; and
      a sensor configured to output signals indicting the movement of the guidewire based on movement of the at least one movable element;
   a measurement module configured to determine a distance that the guidewire moves in the measurement assembly based on the signals output by the sensor indicating the movement of the guidewire; and
   a location module configured to determine a position of the guidewire based on the distance that the guidewire moves determined by the measurement module.

2. The system as recited in claim 1, further comprising:
   an image processing module configured to process information for generation of a virtual image of the guidewire based on the position of the guidewire determined by the location module.

3. The system as recited in claim 1, wherein the at least one movable element comprises at least one of a rotating belt, wheels, rollers or balls.

4. The system as recited in claim 1, wherein the at least one movable element comprises at least one cam and the sensor comprises a shape-sensing optical fiber which is configured to be deflected by the at least one cam when the guidewire is advanced or retracted in the shape-sensed catheter; and
   wherein the measurement module receives signals from the shape-sensing optical fiber concerning deflections of the shape-sensing optical fiber by the at least one cam for determining the distance the guidewire moves.

5. The system as recited in claim 4, wherein:
   the measurement assembly is configured to receive the shape-sensed catheter; and
   the shape-sensing optical fiber of the shape-sensed catheter comprises the shape-sensing optical fiber that is configured to be deflected by the guidewire when the guidewire is advanced or retracted in the shape-sensed catheter.

6. The system as recited in claim 1, wherein:
   the at least one moveable element of the measurement assembly comprises a torquer configured to be secured to a fixed position on the guidewire, the torquer including a shape-sensing optical fiber; and
   the location module is configured to receive shape sensing information from the shape-sensing optical fiber of the torquer and the shape-sensed catheter, and to determine a position and orientation of the torquer relative to the shape-sensed catheter.

7. The system as recited in claim 1, wherein:
   the at least one moveable element of the measurement assembly comprises a torquer configured to be secured to a fixed position on the guidewire; and
   at least one tracking device associated with the torquer and the shape-sensed catheter is configured to track a position and orientation of the torquer and the shape-sensed catheter to determine a position and orientation of the torquer relative to the shape-sensed catheter.

8. The system as recited in claim 1, wherein sensor of the measurement assembly includes an optical tracking device configured to monitor the movement of the guidewire, and to output the signals indicating the movement of the guidewire.

9. The system as recited in claim 8, wherein the guidewire includes markers and the optical tracking device is configured to read the markers to monitor the movement of the guidewire and/or to calibrate the optical tracking device.

10. The system as recited in claim 2, wherein:
    the image processing module is configured to store a model of the guidewire and to generate the virtual image based on the model;
    the image processing module is configured to position the virtual image by placing a distal tip of the model at a most distal position of the guidewire that is detected by the location module; and
    the image processing module is further configured to update the position of the guidewire based on the distance that the guidewire moves in the measurement assembly.

11. The system as recited in claim 2, further comprising:
    an imaging system configured to acquire images of the shape-sensed catheter and the guidewire;
    a segmentation module configured to segment an image of a portion of the guidewire that protrudes from a distal tip of the shape-sensed catheter to provide segmented data;
    wherein the image processing module is configured to generate a portion of the virtual guidewire that protrudes from the distal tip of the shape-sensed catheter based on the segmented data and 3D knowledge of the distal tip of the shape-sensed catheter.

12. The system as recited in claim 2 wherein the image processing module is configured to display a probabilistic map for a portion of the virtual guidewire that protrudes from the distal tip of the shape-sensed catheter.

13. A method for determining the position of a guidewire, comprising:

receiving the guidewire in a lumen of a catheter including a shape sensing optical fiber;

receiving at least a portion of the guidewire and/or the catheter in a measurement assembly;

monitoring movement of the guidewire in the measurement assembly by providing at least one movable element configured to move in response to the guidewire being advanced or retracted in the catheter, and outputting signals indicating the movement of the guidewire based on movement of the at least one movable element;

determining a distance that the guidewire moves in the measurement assembly based on the output signals indicating the movement of the guidewire; and determining a position of the guidewire based on the distance that the guidewire moves in the measurement assembly.

14. The method recited in claim 13, further comprising:

generating a virtual image of the guidewire based on the determined position of the guidewire; and displaying a probabilistic map for a portion of the virtual guidewire that protrudes from the distal tip of the catheter.

15. A system for determining a position of a guidewire, comprising:

a guidewire;

a shape-sensed catheter including a shape sensing optical fiber and having a lumen, wherein the guidewire is received in the lumen;

a measurement assembly configured to receive at least a portion of the guidewire and/or the shape-sensed catheter, and to monitor movement of the guidewire, wherein the measurement assembly comprises:

at least one movable element configured to move in response to the guidewire being advanced or retracted in the shape-sensed catheter; and a sensor configured to output signals indicting the movement of the guidewire based on movement of the at least one movable element;

at least one processor; and a non-transitory memory storing instructions that, when executed by the at least one processor, cause the at least one processor to:

determine a distance that the guidewire moves in the measurement assembly based on the signals output by the sensor; and determine a position of the guidewire based on the determined distance that the guidewire moves.

16. The system as recited in claim 15, wherein the plurality of movable elements comprise at least one of a rotating belt, wheels, rollers or balls.

17. The system as recited in claim 15, wherein the plurality of movable elements comprise at least one cam, and the sensor comprises a shape-sensing optical fiber configured to be deflected by the at least one cam when the guidewire is advanced or retracted in the shape-sensed catheter; and wherein the at least one processor receives signals from the shape-sensing optical fiber concerning deflections of the shape-sensing optical fiber by the at least one cam for determining the distance the guidewire moves.

18. The system as recited in claim 15, wherein the sensor of the measurement assembly comprises an optical tracking device configured to monitor the movement of the guidewire, and to send the signals to the at least one processor indicating the movement of the guidewire.

* * * * *